(12) United States Patent  (10) Patent No.: US 8,820,324 B2
Smith et al.  (45) Date of Patent: *Sep. 2, 2014

(54) HINGED DRY POWDER INHALER COMPRISING A CIRCULATING AIRFLOW CHAMBER

(75) Inventors: Simon James Smith, Hertford (GB); David Stuart Harris, Milton (GB)

(73) Assignee: Cambridge Consultants Limited (GB)

( * ) Notice: Subject to any disclaimer, the term of this patent is extended or adjusted under 35 U.S.C. 154(b) by 1308 days.

This patent is subject to a terminal disclaimer.

(21) Appl. No.: 12/304,900

(22) PCT Filed: Jun. 13, 2007

(86) PCT No.: PCT/GB2007/002198
§ 371 (c)(1),
(2), (4) Date: Jul. 7, 2009

(87) PCT Pub. No.: WO2007/144614
PCT Pub. Date: Dec. 21, 2007

(65) Prior Publication Data
US 2010/0000531 A1  Jan. 7, 2010

(30) Foreign Application Priority Data
Jun. 13, 2006 (GB) .................. 0611656.0

(51) Int. Cl.
*A61M 15/00* (2006.01)
*B65D 83/06* (2006.01)

(52) U.S. Cl.
CPC ....... *A61M 15/0028* (2013.01); *A61M 15/0008* (2014.02); *A61M 2202/062* (2013.01); *A61M 2206/16* (2013.01); *A61M 2202/064* (2013.01); *A61M 2205/195* (2013.01); *A61M 15/0043* (2014.02); *A61M 15/0021* (2014.02); *A61M 2205/197* (2013.01); *A61M 2209/06* (2013.01); *A61M 15/002* (2014.02); *A61M 15/0045* (2013.01); *A61M 15/0036* (2014.02)
USPC ............. 128/203.21; 128/203.12; 128/203.15

(58) Field of Classification Search
USPC ............. 128/203.12, 203.15, 203.19, 203.21, 128/203.23, 203.25
See application file for complete search history.

(56) References Cited

U.S. PATENT DOCUMENTS 3,980,074 A    9/1976  Watt et al.
4,155,359 A *  5/1979  Zagorski .................. 128/206.15

(Continued)

FOREIGN PATENT DOCUMENTS

EP    129985 A1 *  1/1985
FR    2352556      5/1976

(Continued)

OTHER PUBLICATIONS

International Search Report PCT/GB2007/002198 Dated Sep. 25, 2007.

(Continued)

*Primary Examiner* — Tan-Uyen T Ho
*Assistant Examiner* — Kathryn E Ditmer
(74) *Attorney, Agent, or Firm* — Cantor Colburn LLP (57) ABSTRACT

A dry powder inhaler comprises two parts (2, 4) connected by an integrally molded, e.g. living hinge (6), so as to be moveable from an open position to a closed position. At least one of the parts (2, 4) defines at least part of a circulating airflow chamber (12), wherein when said parts (2, 4) are in said closed position, the inhaler comprises an airflow path including the circulating airflow chamber (12).

19 Claims, 9 Drawing Sheets

(56) References Cited

U.S. PATENT DOCUMENTS

| | | | |
|---|---|---|---|
| 5,070,870 A * | 12/1991 | Pearce | 128/203.15 |
| 5,881,719 A * | 3/1999 | Gottenauer et al. | 128/203.15 |
| 6,367,473 B1 * | 4/2002 | Kafer | 128/203.21 |
| 6,606,992 B1 * | 8/2003 | Schuler et al. | 128/203.15 |
| 6,915,802 B1 * | 7/2005 | Anderson et al. | 128/203.15 |
| 2002/0092523 A1 * | 7/2002 | Connelly et al. | 128/203.15 |
| 2003/0196654 A1 * | 10/2003 | Stein | 128/200.23 |
| 2004/0118399 A1 * | 6/2004 | Young et al. | 128/203.15 |
| 2009/0032427 A1 * | 2/2009 | Cheu et al. | 206/438 |

FOREIGN PATENT DOCUMENTS

| | | |
|---|---|---|
| GB | 2179260 | 3/1987 |
| GB | 2380410 | 4/2003 |
| GB | 2420982 | 6/2006 |
| WO | 8907464 | 8/1989 |
| WO | 9913930 | 3/1999 |
| WO | 2004054646 | 7/2004 |
| WO | 2006030459 | 3/2006 |
| WO | 2006061637 | 6/2006 |
| WO | 2007042822 | 4/2007 |

OTHER PUBLICATIONS

UK Search Report GB0711432.5 Dated Sep. 13, 2007.

\* cited by examiner

| Configuration | A | B | C | D | E |
|---|---|---|---|---|---|
| Sketch | f10, 14, 14 | 3.9, f14, 7, 20 | 4.7, f17, 8.6, 24.3 | 5.5, f20, 10, 28.6 | 3.9, f14, 7, 28 |
| Objective | Multi-dose | Small cut point | Medium cut point | Largest cut point | Elongated 2:1 aspect ratio |
| Diameter (mm) | 10 | 14 | 17 | 20 | 14 |
| Length (mm) | 14 | 20 | 24.3 | 28.6 | 28 |
| Cut-off dia (mm) | TBC | 3~4 | 4~5 | 5~6 | 3~4 |
| D P (Pa) | TBC | 61 | 25 | 12 | 21 |

FIG. 9

| Device Type | Flow Rate (l min$^{-1}$) | % Active in Formulation | Fine Particle Fraction (%) | Mean Mass Aerodynamic Diameter (μm) |
|---|---|---|---|---|
| Conventional DPI 1 | 28.3 | 15 | 34.53 | 3.85 |
| Conventional DPI 2 | 28.3 | 15 | 37.31 | 3.79 |
| Cyclone E | 28.3 | 15 | 75.73 | 2.44 |
| Cyclone D | 28.3 | 15 | 79.10 | 2.56 |
| Cyclone C | 28.3 | 15 | 80.60 | 2.31 |
| Cyclone B | 28.3 | 15 | 78.65 | 2.39 |
| Cyclone A | 23.0 | 15 | 69.15 | 2.65 |

FIG. 10

HINGED DRY POWDER INHALER COMPRISING A CIRCULATING AIRFLOW CHAMBER

This invention relates to inhalers for delivering substances in powder form to the respiratory system of a user by inhalation.

Dry Powder Inhalers (DPIs) are conventionally used to deliver active drug substances to the lungs of a user to treat asthma and other respiratory diseases. The basic principle upon which such inhalers work is that the user holds the inhaler to his or her mouth and draws breath through the device, thereby setting up a flow of air which entrains drug particles so that they are drawn into the user's respiratory system. The drug may be in the form of a free powder, or more commonly the drug is bound to carrier particles such as lactose. Of course, a blend of drug particles may be used.

The combined, aggregate particle size of the drug particle and carrier particle is generally greater than 1-5 µm (microns) which is the target size range for particles to be effectively inspired into the deep part of the lungs. DPIs therefore need to de-aggregate the particles (that is to separate the drug particles of respirable size from the larger carrier particles).

Furthermore, there is a tendency for the respirable particles to aggregate during storage. The DPI should there to de-aggregate these fine (respirable) particles. Despite this, known DPIs are rather inefficient at de-aggregating the drug particles. The number of particles of respirable size as a proportion of the total output of the inhaler is known as the Fine Particle Fraction (FPF). In typical conventional inhalers, the Fine Particle Fraction can be as low as 30% and 40-50% is typical. Moreover, in many devices the FPF is dependent upon the inhalation flow rate of the user so that performance is inconsistent both between users and from one use to the next. Of course, a low FPF also leads to much of the drug being wasted. The additional problem with the FPF being inconsistent is that it is then impossible to control the dose actually being received by the user.

A low FPF is of particular concern since the particles which are not fully inhaled tend to hit the back of the user's throat and are deposited there. There is some evidence to suggest a link between deposition of steroid-based drugs on a user's throat and an increased risk of throat or lung cancer.

A further problem with existing dry powder inhalers is that the carrier particles (e.g. lactose) also tend to be inhaled and hit the back of the throat which gives rise to an unpleasant gritty feel. The build up of lactose also can be a contributing factor towards thrush.

Conventional DPIs are usually susceptible to moisture which can affect both the FPF and the delivered dose consistency. Even if the inhaler is provided with a cover, it must be opened to use and/or refill the inhaler.

There have been several proposals in the art for arrangements in which the Fine Particle Fraction is increased. However, these devices often have several other drawbacks. Firstly, they require active systems such as pressurized air which means that they are complex and therefore expensive to manufacture; and bulky and inconvenient to use. As they typically require significant manual force to be applied before inhalation, they take longer to use and cannot be used by those with impaired dexterity. Prior art arrangements also tend to be operable only in a particular orientation.

Some inhalers include a circulation chamber designed to set up a swirling airflow which separates out fine particles using centrifugal forces. Such swirl chambers tend to make the inhaler rather large.

Existing designs also suffer from the problem of particles being deposited on the walls of the inhaler itself. Whilst deposition on the apparatus is preferable to deposition on the back of the throat, it can give rise to a further problem when the deposited powder is dislodged in a subsequent use since this will adversely affect the uniformity of dose received by a user.

It is an object of the invention to provide an improved dry powder inhaler which alleviates at least some of the problems set out above.

When viewed from a first aspect the present invention provides a dry powder inhaler comprising two parts connected by an integrally moulded hinge so as to be moveable from an open position to a closed position, at least one of said parts defining at least part of a circulating airflow chamber, wherein when said parts are in said closed position, the inhaler comprises an airflow path including the circulating airflow chamber.

Thus it will be seen by those skilled in the art that in accordance with the invention there is provided an inhaler which defines a circulating airflow chamber in its closed position. When the inhaler is closed and a user inhales powdered medicament can be entrained in the airflow and de-aggregated in the chamber. This arrangement has the advantage of being able to be manufactured very cheaply since a single moulding can replace most, if not all, parts of a conventional inhaler.

Although the inhaler may be re-useable, such an inhaler is ideally suited for administration of a single dose of medicament powder and subsequent disposal. This might be one in a regular series or course of doses, in which case it is advantageous in overcoming the problem of deposition affecting dose content uniformity that can be encountered in known multi-dose inhalers A single use device is also more hygienic generally and removes any tendency for users to share the same inhaler.

Even more beneficially though, a single dose inhaler may be found particularly suitable for one-off treatment of medical conditions, for example in administering an antidote, vaccination or immunisation, especially where it is necessary to carry this out for a large number of people, such as in the event of an outbreak of a health epidemic.

The powder to be inhaled could be provided separately, e.g. in a dose carrier, and introduced into the inhaler when required, but preferably the powder is pre-provided in the inhaler. Preferably the powder remains in a sealed compartment until ready to be taken so that both the inhaler and the dose are provided together ready for use. This prevents the ingress of moisture, contamination etc. Most preferably the seal is broken by the action of closing the inhaler prior to use. After use the inhaler can simply be discarded.

It will be understood that what is meant by a circulating airflow chamber is any kind of chamber which creates a circulating, swirling or turbulent airflow that acts to de-aggregate entrained powder particles. However, in particularly preferred embodiments the circulating airflow chamber has an air inlet and is so shaped that at least a part of the chamber decreases in cross-sectional area in a direction away from the air inlet, so as thereby in use to set up a reverse flow cyclone in the chamber.

Thus it will be seen by those skilled in the art that in accordance with such preferred embodiments the user's breath is drawn through an airflow path which includes a reverse-flow cyclone chamber. The airflow passes through the cyclone chamber, setting up a reverse-flow cyclone. The required powdered substance is entrained either before or during the passage through the chamber. The reverse flow cyclone referred to herein has a particular meaning distinct from the general usage of the term cyclone in the art to mean any form of circulating air. A reverse-flow cyclone is one in which the air circulates in two, generally concentric, columns in opposite axial directions.

This arrangement is particularly advantageous in the present application for a number of reasons.

Firstly, the flow pattern in a reverse flow cyclone—with an outer, downwardly spiralling "free" vortex and an inner, upwardly spiralling "forced" vortex—gives rise to a substantial fluctuation in tangential velocity across the width of the chamber. The steep velocity gradient encountered in the flow cause efficient de-aggregation of the particles. Moreover, the particles are subjected to these relatively high shear forces both as they travel downwardly to the base of the chamber and also as they travel back up the chamber in the inner, forced vortex. This relatively long flow path over substantially the whole of which de-aggregation can take place leads to a significantly increased proportion of fine particles within the entrained airflow as it travels towards the exit of the cyclone chamber.

Secondly, the central, forced vortex, which travels up from the base of the chamber is relatively tight and well defined. As is known in the art, the mean radius of circulation of a particle is dependent upon its weight and therefore size. Thus by careful selection of a particular circulation radius, a very sharp cut-off threshold of particle sizes may be achieved. By selecting a radius equivalent to 5 microns or less, an even higher Fine Particle Fraction may be achieved. Such selectivity can be obtained for example, by a "vortex finder" comprising a tube projecting some way into the cyclone chamber, which provides the outlet to the chamber.

Thirdly, the reversal of vertical direction of travel of the particles at the base of the chamber causes the de-aggregated carrier particles, and any drug or combination particles which are too large, to be trapped within the cyclone and thus not be inhaled by the user. This substantially reduces the deposition of large particles on the user's throat with the attendant problems referred to previously. The separation of the large particles retained in the inhaler from the finer particles which are inhaled is seen as an important benefit which may be achieved in accordance with some preferred embodiments.

The reversal of vertical direction of travel at the base of the chamber also produces a toroidal flow pattern which aids mixing and de-agglomeration.

Fourthly, the residence time of the particles is greatly increased (therefore giving a greater number of opportunities for separation). Typically in a conventional DPI all drug is evacuated within 0.5 seconds. In accordance with preferred embodiments of the invention, particles remain within the device for the full duration of inhalation. This maximizes the shear forces for a given energy input.

Fifthly, where carrier formulations are used, it has been found that the heavy carrier particles are thrown to the outside of the free vortex where they collide with the chamber walls. These collisions aid the de-agglomeration of drug particles from carrier particles. While the heavy carrier particles continue to rotate at the outside of the free vortex, the lighter drug particle aggregates move into the shear zone between the outer free vortex and the inner, upwardly spiralling forced vortex where they are broken up further. This two-stage process results in a very high Fine Particle Fraction with the majority of the carrier particles remaining in the cyclone chamber rather than being inhaled.

A reverse flow cyclone chamber therefore provides significant advantages over conventional circulation or swirl chambers. In particular, efficient de-aggregation can be achieved in a reverse flow cyclone chamber which is relatively small in size compared to known swirl chambers as the entrained particles are subjected to the shear forces produced at the boundary between the outer, free vortex and the inner, forced vortex. This allows a reduction in size of the overall inhaler which can make it particularly suitable for handheld use. An inhaler in accordance with preferred embodiments can therefore be made small enough to be carried in the pocket while still achieving a high FPF.

In general, the outlet from the chamber will be provided at approximately the same level as below the air inlet. This maximizes the benefit given by the reverse cyclone flow pattern.

When viewed from a further aspect the invention provides a dry powder inhaler comprising: an airflow path including a cyclone chamber having an air inlet and being so shaped that at least a part of the chamber decreases in cross-sectional area in a direction away from the air inlet, so as thereby in use to set up a reverse flow cyclone in the chamber; said inhaler comprising two parts connected together by an integrally moulded hinge defined by a line of weakness.

Where a reverse-cyclone chamber is provided, the decreasing cross-sectional area could be achieved in a number of ways. To give one example, the chamber could be generally cylindrical with a conical or frusto-conical inward protrusion from the base thereof to give the reducing internal cross-sectional area which gives rise to the reverse-cyclone flow pattern described previously. Preferably, however, the outer wall of the chamber tapers towards the base. This could be a curved taper, but preferably the shape is generally frusto-conical. This has been found to give the most efficient reverse-cyclone flow pattern.

The chamber including its air inlet will be arranged so that the necessary vortex is set up when a user inhales. Although there are other ways of achieving this, preferably the air inlet is directed substantially tangentially. Preferably the air inlet is arranged to direct air in such a way that it circulates around the periphery of the chamber. Preferably the chamber has a cylindrical section in the region of the air inlet. This facilitates establishment of the free vortex airflow. Of course there could be more than one air inlet.

The two parts of the inhaler may each define a part of the circulating airflow or reverse-cyclone chamber such that the complete chamber is not formed until the parts are closed together. However this is likely to require stringent moulding tolerances. Preferably therefore the chamber is formed integrally with or permanently attached to one of the inhaler parts. For example, the circulating flow chamber could be provided by a separate part which is snap-fitted onto one of the parts of the inhaler, or otherwise irremovably attached. This might be the case where the powder dose is provided on the same part, e.g. in the chamber. In the context of a device intended for single-use this may be beneficial as it keeps the separate part in the device for disposal and ensures that the inhaler cannot be reused. Most preferably though the chamber is formed integrally with one part of the inhaler to simplify manufacture, supply and use.

Preferably a mouthpiece is formed integrally with one or both of the hinged parts. Again it may not be formed until the two parts are hinged to their closed position but preferably it is formed on one part. When the inhaler is designed for single use there is no need for additional parts such as a mouthpiece cover, multiple dose cartridge, dose counter, etc. Hence it is preferred that the whole inhaler is integrally moulded in one piece in order to minimise production and supply costs. This is novel and inventive in its own right and hence when viewed from another aspect, the present invention provides a dry powder inhaler integrally moulded in one piece which comprises a line of weakness defining a hinge to allow two parts of the inhaler to hinge between an open position and a closed position.

Although alternatives are envisaged, such as a mesh which de-aggregates powder as it passes through, preferably the inhaler of the foregoing aspect of the invention comprises a circulating airflow chamber.

It will be seen by the skilled person that by providing a line of weakness in the material a hinge is formed without requiring an assembly of separate parts. This allows the inhaler to be manufactured cheaply and easily but with the functional benefits of selective opening and closing of the two parts.

It is preferred that an inhalation airflow path through the inhaler is only formed when the two parts are closed together.

As before, preferably the inhaler comprises a dose of powder, preferably in a sealed compartment thereof. The dose may be released, exposed or otherwise made available by user intervention prior to inhalation, for example by removing a foil or polymeric film seal protecting the dose which is not part of the main moulding or by opening a dose holder. In one set of preferred embodiments the dose is held in a chamber with a grommet cover extending partly over said chamber and defining an aperture above the chamber; and a protective layer covering at least said aperture wherein the edge of the grommet cover defining the aperture is compliant so as in use to form a seal around a tube passing through the aperture. In such embodiments the protective layer is removed and then act of closing the two parts of the inhaler will cause a tube to pass into the dose chamber whilst maintaining a seal around it.

In other embodiments a sealing membrane is left in place and the dose is released by the act of closing the two parts of the inhaler together. This may be achieved by one or more piercers being provided on one of the parts and a sealed dose being provided on the other part. Upon moving the hinged parts together, the piercer(s) break the seal such that the dose can be exposed to an air flow for inhalation. Preferably the inhaler comprises an airflow inlet and an airflow outlet to the dose chamber which are integrated with piercers.

The air inhaled by a user may all be drawn through the circulating airflow/reverse cyclone chamber. However in accordance with preferred embodiments of the invention the inhaler comprises a main airflow path which passes through the chamber and a bypass airflow path bypassing the chamber; wherein the main and bypass airflow paths communicate with the mouthpiece.

In accordance with such embodiments, only a proportion of the air inhaled by a user is drawn through the circulating airflow chamber. The remainder is drawn through the bypass airflow path into the mouthpiece without passing through the chamber. The Applicant has found that such bypass airflow can be important in limiting the flow rate through the chamber, and controlling the overall device airflow resistance as felt by the user. Particularly where, as is preferred, the circulating airflow chamber is a reverse cyclone chamber. If there is too great a flow rate through the circulating airflow chamber, then the velocity of the particles is too great and so even the fine respirable particles are separated and hence retained in the cyclone. Therefore the cyclone must be sufficiently large to allow the respirable particles to escape for a given flow rate. In practice this could mean that the chamber would be too large to be incorporated in an easily portable device such as can be carried in a pocket or handbag.

However by using the bypass, the flow rate through the chamber may be limited without having to increase the overall inhalation resistance of the inhaler, which would undesirably increase the time required for a user to draw a full breath through the device.

The relative resistances of the main and bypass airflow paths may be set during manufacture so as to give a predetermined flow rate through cyclone at a standard average inhalation flow rate. This has been found to give good results. However, it is envisaged that it might be possible to increase even further the consistency of the Fine Particle Fraction and the delivered dose by providing means for varying the flow resistance of the bypass air flow path such that said resistance is decreased at increasing inhalation flow rates. In accordance with such a feature, the flow rate through the cyclone chamber may be kept more consistent even in the face of a varying rate of inhalation by the user since the resistance in the bypass path will automatically adjust with the user's rate of inhalation. For example, if the user inhales harder than average, the resistance in the bypass airflow path will decrease thereby allowing a greater bypass airflow to meet the excess flow rate without increasing the flow rate through the cyclone chamber to the same extent or, ideally, at all.

The above mentioned variable flow resistance in the bypass path could be achieved in a number of ways. In a simple example, one or more resiliently biased flaps could be provided extending across all or part of the bypass airflow path. In one convenient embodiment envisaged, a star-valve could be utilized. These generally comprise a plug of resilient material across a tube with a series of radial slits which allow individual segments to flex outwardly thereby allowing fluid to flow past the valve. The characteristics of such valves is that as the flow rate of fluid through them increases, the deflection of the individual segments also increases, thereby enlarging the generally star-shaped aperture which is created. Such a structure is commonly to be found on domestic containers for viscous fluids such as sauces, toiletries etc.

It is not critical to the invention where the bypass air flow and the main airflow meet. For example they could meet inside the inhaler. For example the bypass air flow could simply be provided by an aperture in the mouthpiece. Preferably the main and bypass airflows do not meet at all inside the inhaler. This is achieved by providing a divided mouthpiece, with one channel for the main airflow and the other channel for the bypass airflow. Preferably the bypass airflow is provided via a grille in the body of the inhaler.

In preferred embodiments of the invention the inhaler at least when in its closed position, comprises a cyclone chamber having a cyclone chamber outlet extending substantially axially therefrom; a mouthpiece channel having a central axis; and a plenum portion connecting said cyclone chamber outlet and said mouthpiece channel, the mouthpiece channel axis being offset from, and making a non-parallel angle with, the axis of the cyclone outlet such that in use air exits the cyclone outlet at least partly tangentially into the mouthpiece. This arrangement has been found to reduce the deposition of powder inside the mouthpiece and to reduce the overall flow resistance of the inhaler.

Although so far only embodiments of the invention in which the entrained particles encounter a single circulating airflow chamber have been specifically mentioned, this is not essential. Thus, the inhaler could be provided with two or more circulating airflow chambers. These could be arranged in series with one another, in parallel with one another or a mixture of the two. An example of the latter would be where two or more parallel ante-chambers feed a single downstream chamber or conversely where a single ante-chamber feeds a plurality of downstream chambers. Of course there are many variants possible depending upon the number of chambers provided. One particular possibility is that one or more circulating airflow chambers could be provided on a separate part and one or more further chambers provided integrally with the inhaler. For example, the chamber on the separate part could act primarily to trap carrier particles which would then be discarded along with the disposable part, with subsequent chambers in the inhaler acting primarily to enhance the de-aggregation or selection of respirable particles.

Returning to the shape of the tapering area reverse-cyclone chamber, the Applicant has devised a some possible features whereby performance of the chamber may be enhanced. In some preferred embodiments, the base of the reverse cyclone chamber generally conforms to part of the surface of a toroid, which has been found generally to enhance the establishment of the reverse-cyclone flow pattern, but also more particularly to enhance tight local circulation of the larger particles which are trapped at the base of the cyclone chamber.

In another potential preferred feature, the base of the reverse cyclone chamber is provided with a series of concentric ridges i.e. it has a stepped profile. In some circumstances this can give a more desirable flow pattern.

In another potential preferred feature vertical ridges may be provided in the chamber to enhance the performance.

In yet another possibility, the surface finish of the wall of the chamber could be made rough or smooth as desirable to give an appropriate flow pattern. The surface finish could even vary from rough to smooth or vice versa to influence the particular flow since the Applicant has observed that the roughness of the surface affects the performance of the cyclone. Of course, any combination of the features mentioned above may be employed.

A plurality of doses could be associated with the inhaler, i.e. so that the inhaler is reused a small number of times. For example the inhaler may be provided with a separate dose holder comprising a cartridge of multiple doses. Each of the doses in the cartridge could be taken before replacing the dose holder or discarding the inhaler and dose holder together. It is preferred, however, that only a single dose is associated with the inhaler. Also two or more drug powders could be separately stored and mixed in the circulating airflow chamber e.g. with two or more tangential inlets to the circulating airflow chamber.

Even where the inhaler is integrally moulded as a single piece, the drug or other powder can be provided by a separate dose holder. This would have the advantages mentioned above of isolation of the drug prior to use etc. Whether or not the powder is provided inside the inhaler or by a separate dose holder, the drug is preferably released by the act of closing the two parts together through movement of the integral hinge. For example, where the drug is protected by a frangible membrane, the inhaler could be arranged to pierce this when the inhaler is closed.

Returning to storage of discrete pre-metered doses, in some preferred embodiments these could be provided with a second membrane to isolate them from the rest of the dose chamber or dose holder. This would further enhance the protection against moisture and contamination. This would allow the powder to enter the air stream in a specific region of the airway which may be beneficial to performance. In some preferred embodiments, desiccant means are provided in association with the stored powder dose. One possibility would be to provide desiccant crystals in a physically separate but gaseously communicated pouch. However, a preferred example would be to provide a different layer within a membrane retaining powder.

In accordance with all embodiments of the invention, the dose of powder could be arranged to be introduced into and entrained by the inhaled air at any convenient point in the system. For example, the powder could be stored within the circulating airflow chamber and released at the appropriate time into the chamber. Alternatively, the powder could be introduced into the chamber by the vortex finder where such is provided. Preferably, however, the powder is stored within the circulating airflow chamber and exposed to an entraining airflow in the chamber upon inhalation.

In other arrangements the powder could be entrained prior to entry into the circulating airflow chamber. In some arrangements this could take place in a conduit leading to the chamber, although in an advantageous arrangement a further ante-chamber is provided upstream of the swirl or cyclone chamber into which the powder is delivered. Preferably this ante-chamber is arranged to encourage a circulatory airflow therein. This has the advantage of providing a "scouring/scrubbing" flow to collect powder efficiently from the inner surface of the chamber. It is of particular benefit in applications where the powder particles do not flow very well.

Where the circulating airflow chamber is protected by a frangible membrane, this could be pierced upon installation into the inhaler if a separate circulating airflow chamber pack is used. In at least some preferred embodiments where the circulating airflow chamber is an integral part of the inhaler, the chamber is preferably pierced by the patient when the dose is ready to be taken. Preferably an outlet pipe projects into the chamber to form a vortex finder. The patient may remove a sealing film to allow the vortex finder access to the chamber, but preferably the vortex finder is integrated with a piercer. Where, as is preferred, the vortex finder is provided on one part of the inhaler and the chamber on the other part, the vortex finder may pierce the frangible membrane sealing the chamber when the two parts are closed together. The user may therefore close the inhaler immediately prior to inhalation so that the dose is not uncovered until it is ready to be taken.

The dimensions of the inhaler may be chosen to suit the particular desired application. However the features set out herein are especially advantageous in inhalers which are portable and can be held in one hand. Preferably the diameter of the cyclone chamber is between 5 and 100 mm, more preferably between 5 and 50 mm and most preferably between 8 and 20 mm. It will be appreciated that a reverse cyclone chamber can be made much smaller than conventional circulation or circulating airflow chambers while achieving a high Fine Particle Fraction, resulting in a small yet effective inhaler. The reduced size of the inhaler helps to reduce material costs and makes the preferred embodiment particularly suitable as a low cost, disposable device.

In accordance with all aspects of the invention set out above, the integrally moulded hinge may take any suitable form. The inhaler may be moulded with a line of weakness forming the hinge. This can be achieved by a line of perforations in the material or, preferably, by thinning a line of the material. A hinge so formed is typically known as a living hinge. A flexible plastics material is particularly suitable for forming a living hinge.

The inhaler may be moulded from a plastics material e.g. polypropylene. Such materials are low cost and easily mouldable, and produce a lightweight inhaler which is strong and resistant to environmental conditions, especially the ingress of moisture.

Furthermore the Applicant has appreciated that by providing the inhaler with a hinge, a dose can be stored and protected on one of the parts and then released and/or exposed to entraining airflow only when the two parts are closed together and a user inhales. This can provide a particularly simple and effective way of supplying an inhaler and one or more doses together, ready for use.

Alternatively, the provision of the hinge may be used to facilitate opening and closing of the inhaler in order to install a disposable dose holder. The closing of the inhaler can act, as described above, to release the dose, for example by piercing a membrane on the dose holder.

The inhaler may be held closed by a user but preferably it is provided with a snap fit closure. Such a mechanism helps to ensure that air only enters the inhaler through the designated air inlets upon inhalation, so that the correct airflow is set up. A tight closure also means that the user can move the inhaler to their mouth once the dose has been released without it escaping from the inhaler.

The inhaler can be used to administer many different kinds of powdered medicament and the powder can be placed in the inhaler at the point of use, for example by measuring a dose into the inhaler prior to use. However, it is preferable that a dose is stored in the inhaler before it is supplied to the user. In preferred embodiments the chamber is filled with a dose and sealed before being supplied.

In other embodiments the inhaler may receive a separate dose holder. This allows for the supply of a standard inhaler to medical practitioners or end-users who can then load a dose holder of their choice prior to use, providing for selection of e.g. different medicaments or dose strengths. In this situation the inhaler may be used more than once, with a fresh dose being provided for each inhalation. However, it will be appreciated that an inhaler in accordance with at least some of the preferred embodiments can be replaced cheaply enough that it can be thrown away after a limited number of uses instead of attempting to clean the inhaler.

A preferred embodiment of the invention will now be described, by way of example only, with reference to the accompanying drawings in which.

With reference to FIGS. 1-8, the general construction and operation of a dry powder inhaler in accordance with the invention will be described.

Figure 2:
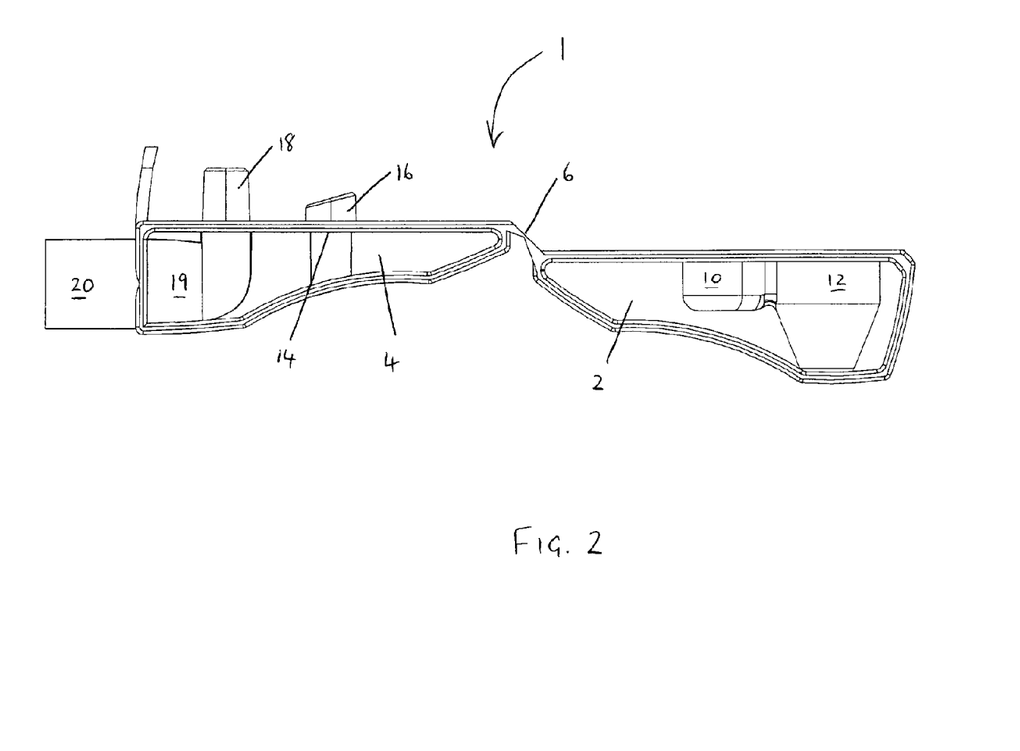
FIG. 2 is a side view of the inhaler in its open position.
Figure 3:
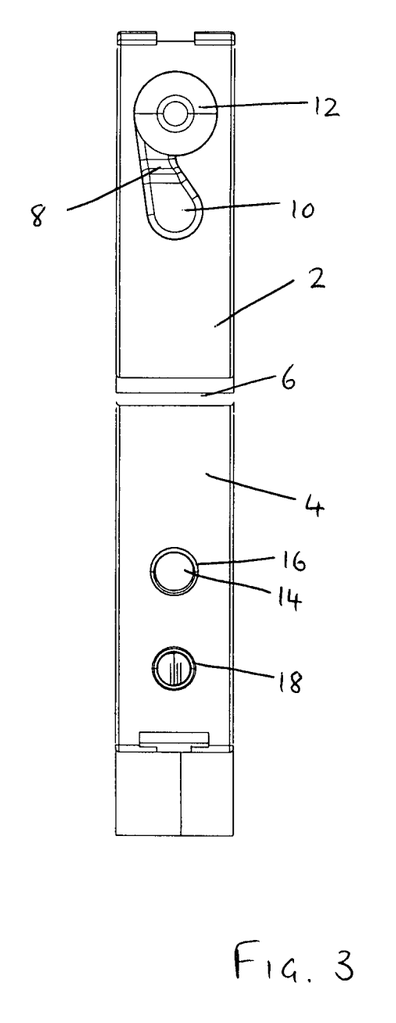
FIG. 3 is a top view of the inhaler in its open position.
Figure 4:
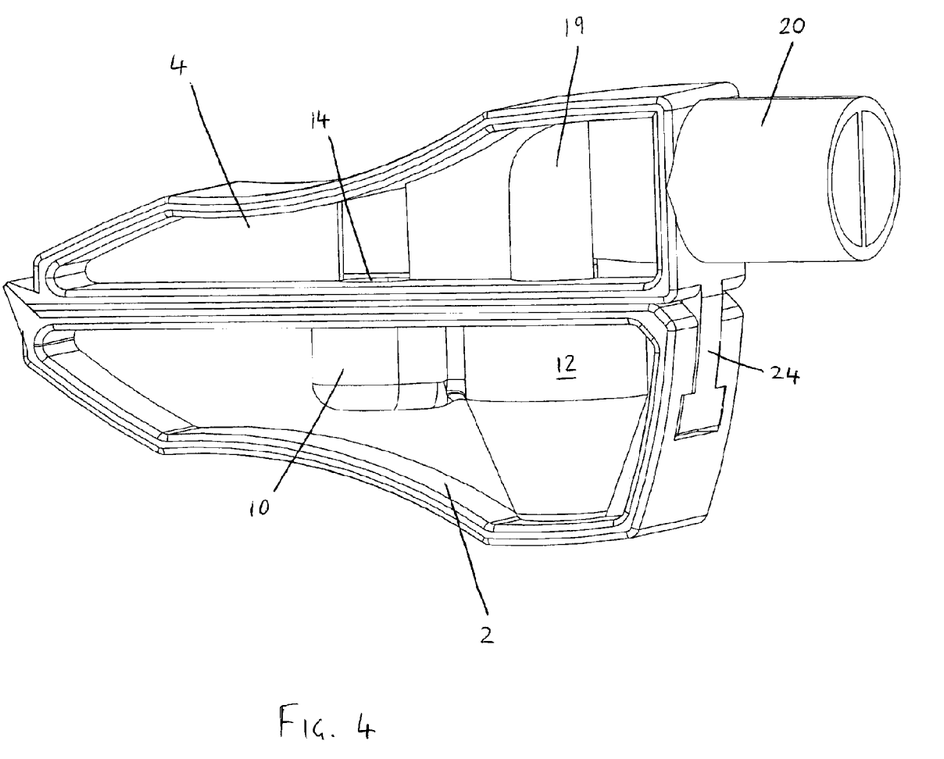
FIG. 4 is a perspective view of the inhaler in its closed position.
Figure 5:
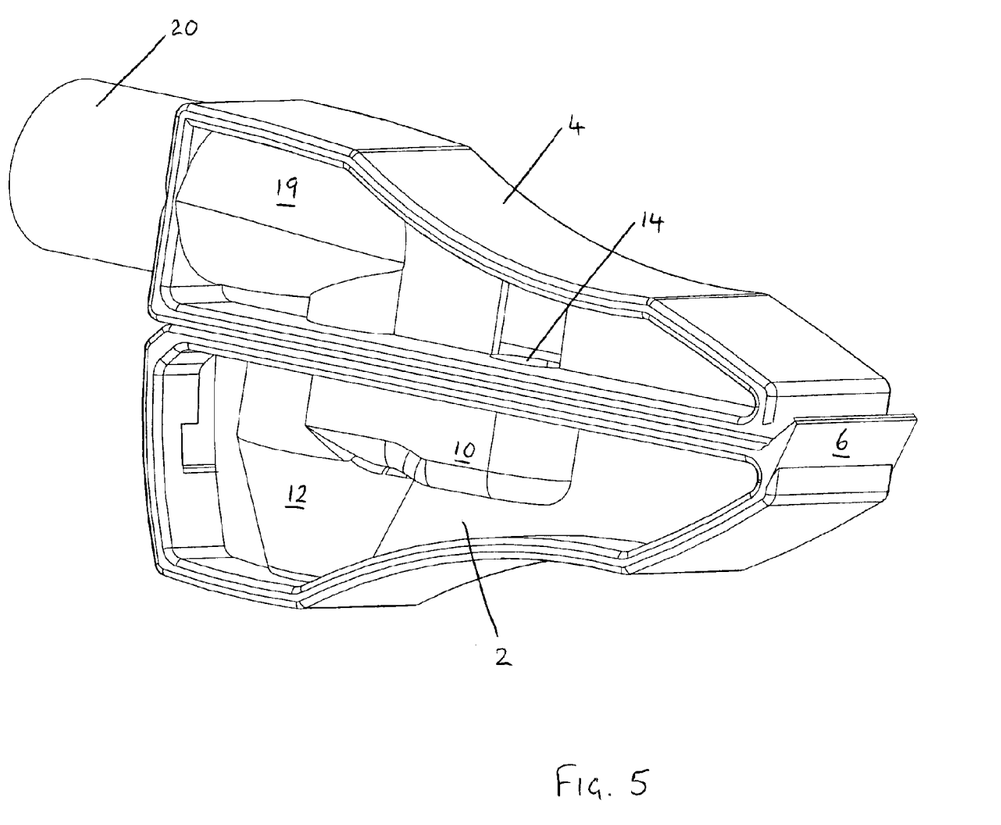
FIG. 5 is a perspective view of one side of the inhaler.
Figure 6:
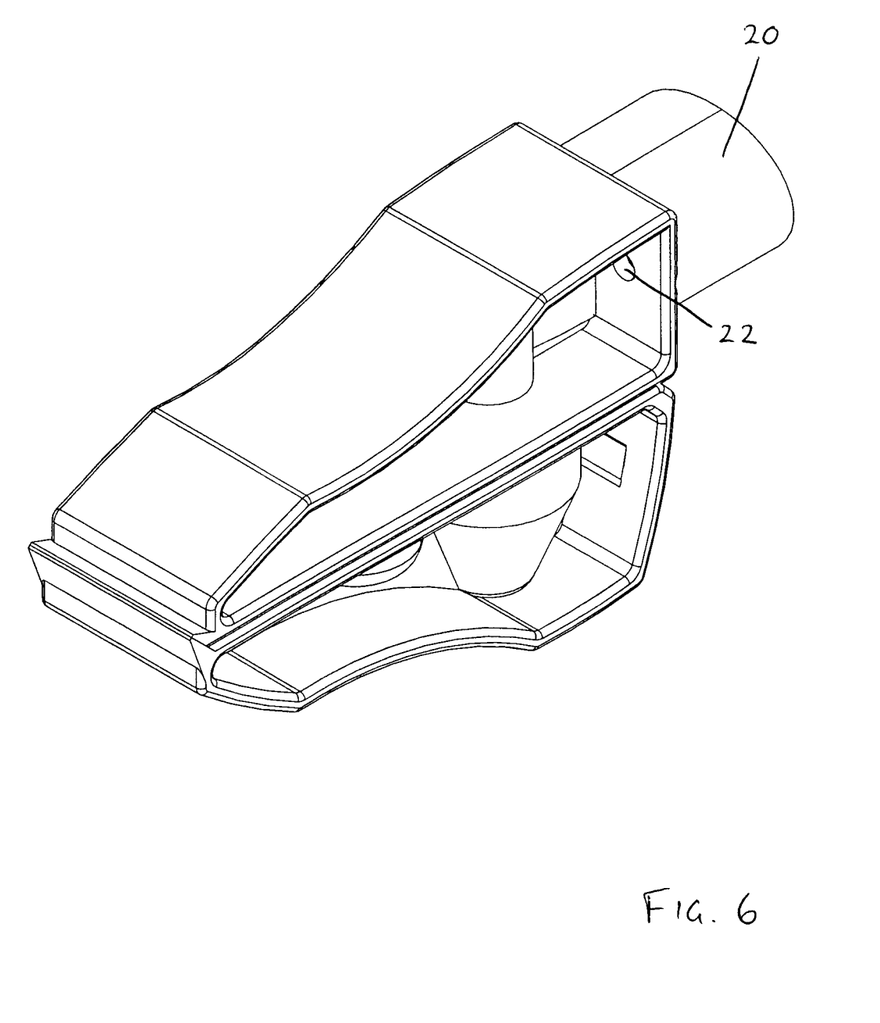
FIG. 6 is a perspective view of the other side of the inhaler.

The inhaler 1 is integrally moulded in two parts from a plastics material such as polypropylene in what is essentially a box-frame structure that gives good strength for minimum amount of material. The bottom part 2 and the top part 4 are connected by a living hinge 6. The hinge 6 is formed by a thinned section of plastic joining the two parts, as is best shown in FIG. 2. The joining section is thinned enough that the two parts can be flexed open and closed, but is strong enough that it retains its mechanical integrity.

In the bottom part 2 of the inhaler there is formed a dose storage and entrainment system 8 which comprises a relatively shallow entrance channel 10 and a circulating airflow or cyclone chamber 12. The entrance channel 10 and cyclone chamber 12 are formed as an integral recess in the bottom part 2. The cyclone chamber 12 is generally cylindrical at its upper end with a frusto-conically shaped base. As can be seen from FIG. 3, the entrance channel 10 is wider at one end and then tapers in towards the point where it connects with the cyclone chamber 12. The entrance channel 10 is configured so as to provide a tangential air inlet into the cyclone chamber 12 at its upper end. The cross-sectional shape and area of the channel 10 at its outlet into the cyclone chamber 12 is chosen so as to promote a well-defined grade efficiency curve in the cyclone chamber 12. This would be optimized on the basis of a specific application.

The inhaler is typically supplied to a user with a single dose of medicament powder held inside the storage and entrainment system 8. The dose may be retained by a plastic film or metallic foil (not shown) covering at least the channel 10 and cyclone chamber 12.

The top part 4 of the inhaler has spaced from its front end, an air inlet conduit 14 which terminates in a protruding inlet tube 16. Closer to the front end of the inhaler an air outlet tube 18 protrudes downwardly. The inlet and outlet tubes 16,18 also act as piercers. In communication with the outlet pipe 18 is a plenum portion 19 which in turn communicates with one channel 20b of an integrally moulded mouthpiece 20. The mouthpiece 20 protrudes forward from the inhaler and is oval-shaped in cross-section so as to fit comfortably in the mouth.

Figure 7:
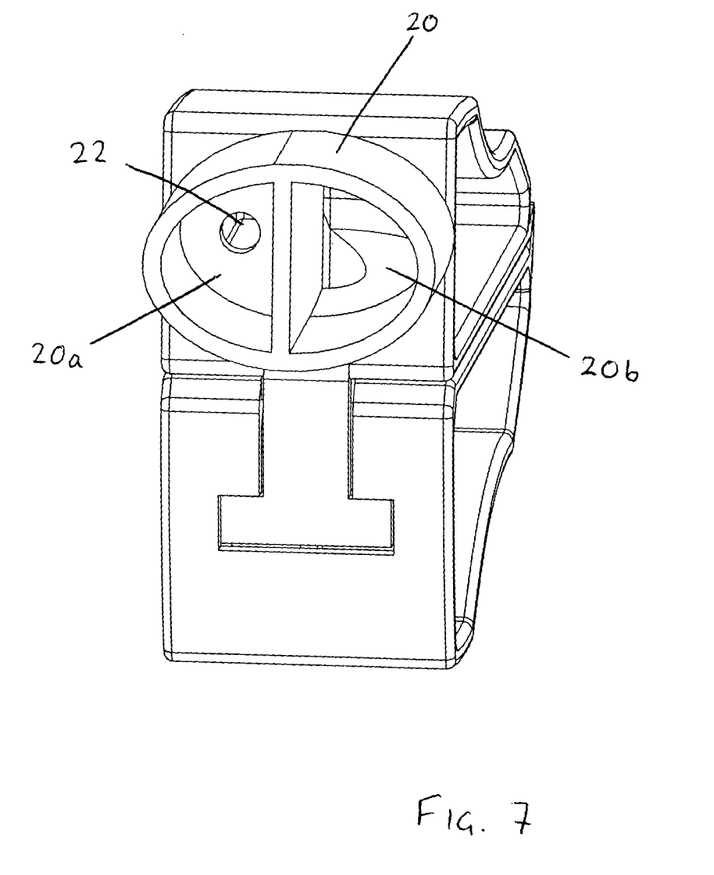
FIG. 7 is a perspective view of the front of the inhaler.

The mouthpiece 20 is shown more clearly in FIG. 7. One channel of the mouthpiece 20a is blocked off apart from an air inlet hole 22. This air inlet 22 provides an airflow directly into the mouth from the exterior, i.e. bypassing the cyclone chamber 12. The other half of the mouthpiece 20b communicates with the plenum portion 19.

The plenum portion 19 is configured so that the central axis of the mouthpiece channel 20b is offset from, and extends at an obtuse angle away from, the cyclone chamber outlet tube 18. Furthermore as can be seen in FIG. 7, the inside of the plenum portion 19 is formed as a smooth scroll section which helps prevent turbulent flow which would increase the risk of powder deposition.

Figure 1:
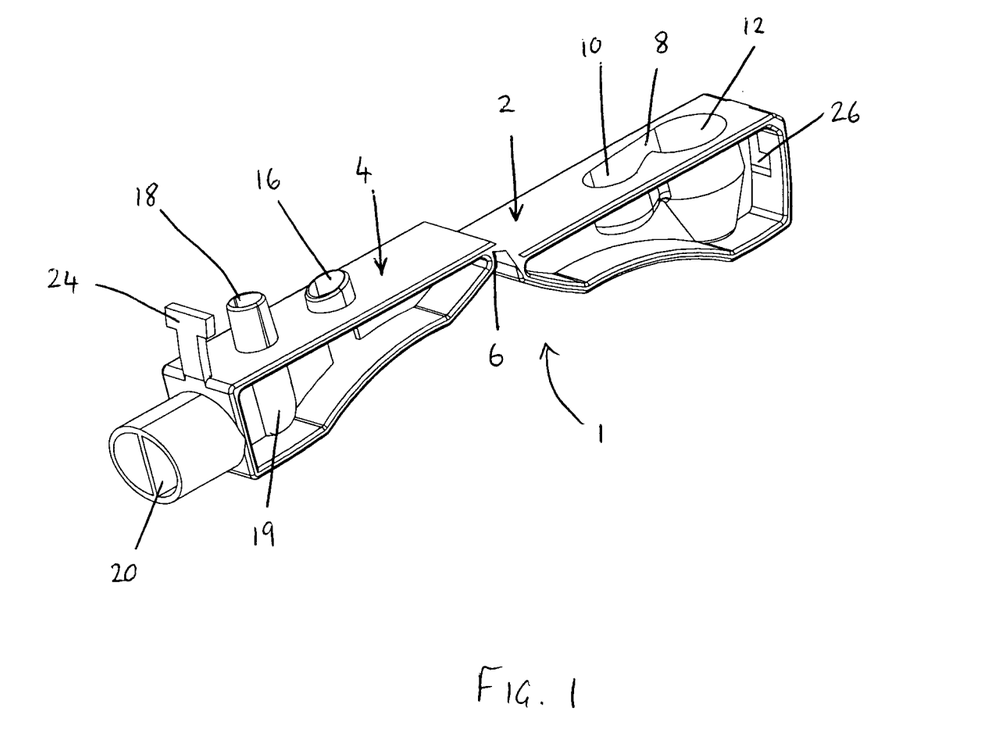
FIG. 1 is a perspective view of an inhaler in accordance with the present invention, in its open position.

As shown in FIG. 1, the inhaler is provided with a snap-fitting arm 24 on the top part 4 and a corresponding recess 26 on the bottom part 2. The inhaler is shown in its closed position in FIG. 4 with the arm 24 snap-fitted into the recess 26 to hold the top and bottom parts together.

Operation of the inhaler will now be described. To prepare the inhaler for use, a user may first have to remove a protective cover from the bottom part 2 where a dose is stored. Protective covers may also be provided over any of the mouthpiece 20, outlet tube 18, and inlet tube 16, so as to prevent the ingress of moisture and contaminant particles into the inhaler airflow path, or more conveniently the whole inhaler can be packaged in a sterile pack. Typically, the bottom part 2 will be sealed from the environment by a frangible membrane such as a metal foil.

When the user is ready to take a dose, he/she first rotates together the top and bottom parts of the inhaler until the arm 24 on the top part 4 snap-fits into the recess 26 on the bottom part 2. A particular advantage of the living hinge 6 is that it allows easy flexing of the parts so that they can be moved together with minimum manual effort and dexterity. The living hinge 6 and snap-fit closure 24,26 together provide a reliable closure mechanism which can be effected even with a relatively clumsy action.

As the inhaler is snapped shut, both the inlet tube 16 and outlet tube 18 protruding from the top part 4 will pierce through any frangible membrane covering the dose storage and entrainment system 8 as the top part 4 is brought together with the bottom part 2. The ends of the inlet and outlet tubes 16, 18 may be sharpened to assist clean penetration of the foil. As the entrance channel 10 is relatively shallow, there is a risk that the pierced foil will impede the movement of air along the channel. To prevent this, the inlet pipe 16 is tapered such that a foil flap is formed and pushed against the back wall of the channel 10 where it does not impede movement of air down the channel. Both piercers are shaped to break open the foil into flaps rather than breaking off foil pieces which will interfere with the airflow in the system and could be harmfully inhaled. In an alternative embodiment (not shown) the bottom part can be covered with a grommet cover defining apertures with compliant edges that do not need to be pierced and which form a seal around the tubes as they pass through. Such an arrangement can avoid the problems referred to above.

Once the inhaler is closed, the user then places the mouthpiece in his/her mouth and inhales deeply. Inhalation draws an airflow through the air inlet conduit 14, down through the inlet tube 16, along the entrance channel 10, into the cyclone chamber 12 where a reverse flow cyclone is set up as is described in more detail below.

With a single dose sealed into the bottom part 4, it may be spread anywhere in the storage and entrainment system 8. Upon inhalation, any of the powdered dose that is laid in the entrance channel 10 will be entrained by the airflow and taken into the cyclone chamber 12. The rest of the powder resides in and is entrained from the chamber itself.

Figure 8:
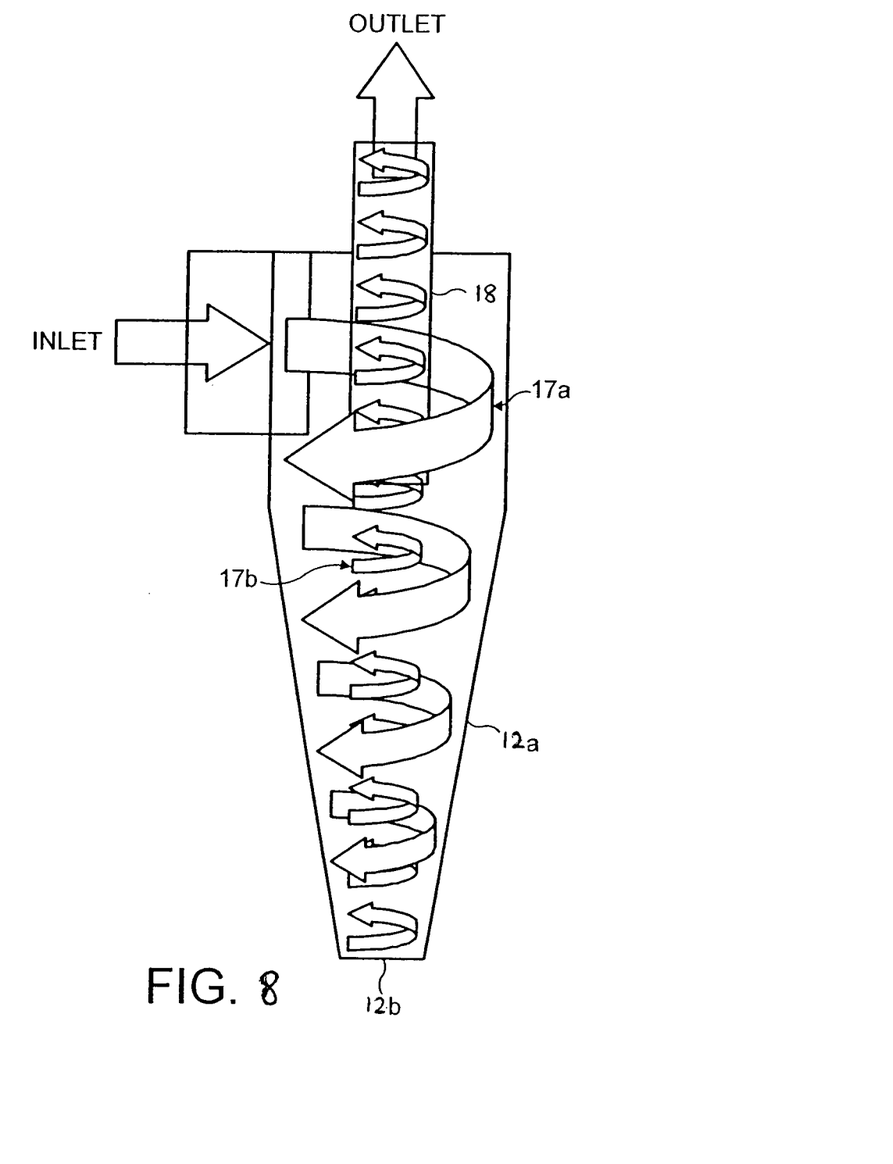
FIG. 8 shows the reverse cyclone airflow in a frusto-conical chamber.

The airflow pattern in the reverse cyclone chamber 12 is shown in FIG. 8. The tangentially entering air and cylindrical upper wall portion set up a bulk circulation of air around the periphery of the chamber 12. The inlet from the communicating channel 10 is also angled down slightly so that the air flow forms a shallow downward spiral known as a "free" vortex 17a. Due to conservation of angular momentum, the rotational velocity of the free vortex increases as the airflow is constricted by the tapering inner surface of the frusto-conical portion of the chamber 12a. As the free vortex 17a hits the base of the chamber 12b it is reflected to form a tight "forced vortex" inside the free vortex and travelling back up the axis of the chamber.

At the top of the chamber 12 the downwardly projecting end of the outlet tube 18 forms a vortex finder. The vortex finder 18 effectively defines a maximum cut-off circulation radius for entrained particles to exit the chamber. Particles circulating at a radius greater than that of the vortex finder 18 will not escape but will either fall back into the cyclone or fall to the base of the chamber 12b.

As entrained powder particles enter the cyclone chamber 12 to be carried downwardly they circulate around the chamber 12 several times. As they travel, the particles experience a shear force arising the from the relatively high spatial velocity gradients that occur when measured across the two vortices 17a, 17b. This shear force tends to de-aggregate and de-agglomerate the particles so that the average size of the particles is reduced and drug particles circulate separately from carrier particles. As mentioned above, some particles may be entrained from the bottom of the chamber.

At the base of the chamber 12b the reversal of direction causes the heavier particles, such as the carrier particles to come out of the main flow to be trapped in eddy currents at the bottom of the chamber or simply to sit at the bottom of the chamber although a toroidal flow pattern is set up at the base of the chamber which aids mixing and de-agglomeration.

The lighter particles which remain entrained travel back up the chamber 12 in the forced vortex 17b giving a further opportunity for de-aggregation. The diameter of the carrier particles is greater than the depth of the boundary layer at the wall of the cyclone chamber and therefore large particles do not remain stationary on the cyclone chamber wall but continue to circulate releasing fine particles throughout the inhalation. Collisions with the chamber walls also help the carrier particles to release the fine drug particles. It will be seen therefore that in contrast to particles being drawn once round a swirl chamber as is known from the prior art, the flow path obtained in accordance with the invention gives a long path through the chamber and so a long residence time which enhances the de-aggregation efficiency, by increasing the number of opportunities the fine particles have to be removed from the carrier particles. The smaller particles with lower momentum circulate at relatively short radii whereas larger particles with greater momentum circulate at larger radii. At the top of the chamber the vortex finder 18 selects the smaller particles, e.g. those of diameter 5 μm or less, with the rest remaining in the chamber 12 as explained above.

The forced vortex air flow exits the cyclone chamber 12 through the vortex finder/cyclone chamber outlet 18 and into the plenum portion 19. The shape of this plenum portion 19 and in particular the fact that the mouthpiece channel 20b is offset from the centre of the circulating flow means that air can continue out along the mouthpiece channel 20b at a tangent to the circulation which minimises the tendency for entrained powder particles to be deposited on the inner surface of the mouthpiece and minimises the flow resistance presented by the inhaler overall. The smooth scroll portion further enhances this since it follows the path naturally followed by the air.

The entrained particles thus exit the mouthpiece channel 20b and into the mouth of the user. The exit chamber 19 diverges as it enters the mouthpiece 20 so as to slow the air flow before it enters the mouth of the user and prevent it from impinging forcefully against the back of the user's throat.

Although the mouthpiece 20 is shown as extending directly forward from the top part 4 of the inhaler, the mouthpiece 20 can be angled upwardly. In particular, the mouthpiece 20 can be set at an angle of about 45°. This ensures that the user holds the inhaler tilted downwardly when they bring the mouthpiece 20 forward towards their mouth, such that the powdered dose in the bottom part will naturally fall into the bottom of the cyclone chamber 12. This helps to ensure that all of the dose is entrained in the reverse flow cyclone for the longest possible time and hence maximises the efficiency of the cyclone.

As the user inhales through the mouthpiece 20, some air will be drawn through the bypass port 22. The main function of the bypass air flow through the inlet 22 is to limit the air flow through the reverse flow cyclone. If the whole of the breath were to be drawn through the cyclone chamber 12 then all of the particles would have a greater velocity and therefore a larger circulation radius and for a given cut-off size (e.g. 5 μm) the diameter of the vortex finder would have to be larger too, in order to allow respirable particles to escape This would require a cyclone chamber too large for incorporation in a convenient hand-held device.

Moreover the bypass air inlet 22 can help to limit the variation in the air flow through the cyclone chamber 12 when the rate of inhalation varies. If the rate of inhalation increases, the bypass air flow also increases, which limits the increase in the air flow in the cyclone and so the tendency for the cyclone to become too efficient, i.e. for the particle cut-off diameter to become too low to deliver the full dose.

The form and dimensions of the bypass air inlet 22 are designed to set the inhaler overall resistance and the proportion of an average breath air flow which passes through the cyclone relative to the bypass air flow. In further embodiments (not shown) the bypass air inlet 22 can include a variable resistance valve such as a resilient star valve which reduces in resistance as air flow through it increases so as substantially to maintain air flow through the cyclone chamber constant. Alternatively, one or more resiliently biased flaps may be provided in the bypass air inlet 22, the extent of opening of the flaps increasing with an increasing rate of inhalation.

By the time the powdered drug enters the user's respiratory system it will generally contain a high proportion of particles of 5 µm or less (i.e. a high Fine Particle Fraction). These can be inhaled into the deep part of the lungs where they will be most effective. Furthermore very little of the drug or carrier is deposited on the back of the user's throat which is beneficial medically and from the point of view of user comfort.

The efficacy of the preferred reverse-flow cyclone arrangement will now be demonstrated using the following examples.

Figure 9:
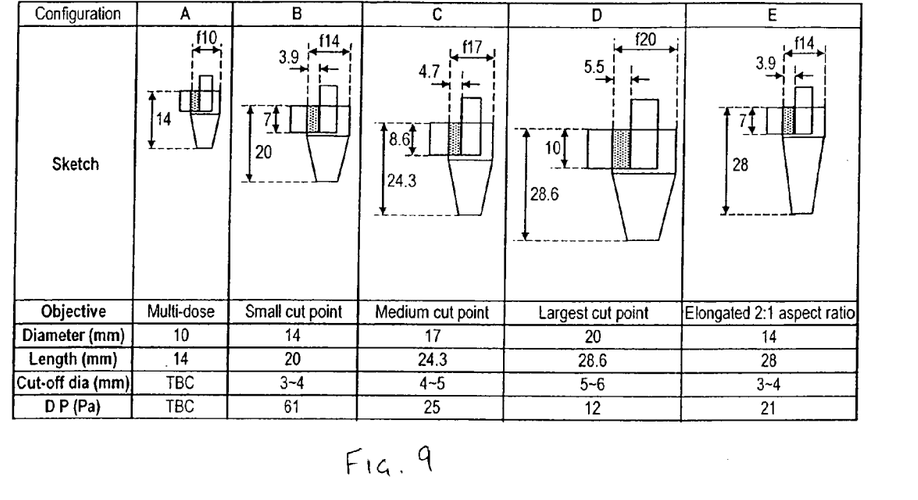
FIG. 9 shows five different cyclone chamber configurations A-E used to test the performance of a reverse flow cyclone.
Figure 10:
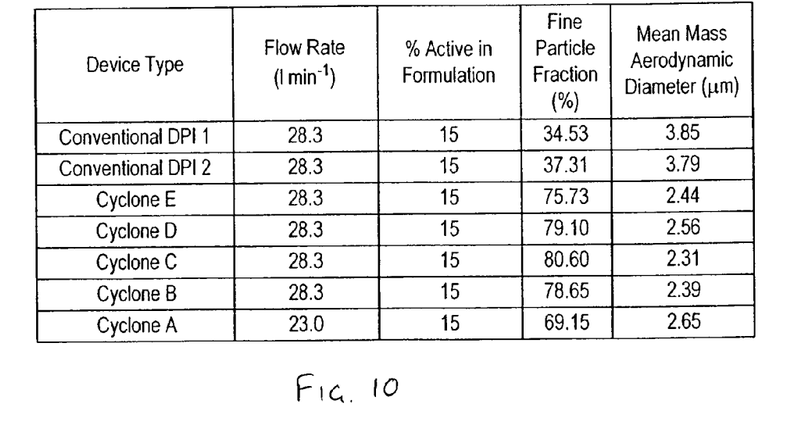
FIG. 10 shows the performance test results for the cyclone chambers A-E of FIG. 9 compared to two conventional dry powder inhalers.

FIG. 9 shows five different cyclone chamber configurations A-E used in a performance test. The cyclone chamber diameters range from 10 to 20 mm. FIG. 10 shows the performance test results for the cyclones A-E compared to two conventional dry powder inhalers. The fine particle fraction achieved using the cyclones A-E is seen to be over 69%, and as much as 81%, compared to only 30-40% for conventional dry powder inhalers. This results from the deposition of large particles above the cut-off size in the base of the cyclone chamber, so that the fine particle fraction is greatly enhanced. The size of the particles separated by the cyclones A-E was also reduced to 2-3 µm in all configurations. Thus cyclone chambers of these configurations separate out particles of a much finer, respirable size than can be achieved by conventional dry powder inhalers, therefore concentration of fine particles in the emitted dose is increased compared to the conventional formulation.

It will be appreciated by those skilled in the art that the embodiment set out above gives a simple and convenient arrangement for a dry powder inhaler in which particles which are too large are retained in the device thus raising the Fine Particle Fraction of what is inhaled and reducing the problems arising with inhaling particles which are too large. Furthermore, because the inhaler is designed to be disposed after a single use, the large particles are discarded. Hence the user will receive a consistently accurate dose from each new inhaler.

Some key features of the preferred embodiment include the following. Firstly, a reverse flow cyclone to efficiently de-aggregate the respirable (fine) drug particles from coarse carrier fraction (e.g. lactose). This is achieved by increasing the residence time of the particles (therefore a greater number of opportunities for separation), and by maximizing the shear forces for a given energy input. Secondly, the reverse flow cyclone separates and retains the coarse carrier fraction—i.e. only respirable (fine) drug particles are emitted upon inhalation. Thirdly the use of bypass airflow to control the separation efficiency of the reverse-flow cyclone, and to tailor the airflow resistance of the device. Fourthly the cyclone geometry being on a disposable device, to maximize Dose Content Uniformity (DCU), by preventing carry-over of drug particles between doses. Fifthly, formulation is pre-metered into a moisture-proof chamber, therefore accurate dose mass, and performance independent of environmental conditions. Finally, a disposable device which retains the non respirable fraction aerodynamically during inhalation and mechanically after inhalation.

Although the above preferred embodiment has been described as having a powdered dose stored and sealed into the bottom part 2 of the inhaler, it will be appreciated that a dose may be stored in either part of the inhaler as long as it is subsequently released and entrained in the main airflow path which includes the reverse flow cyclone chamber. It is not essential for the dose to be stored in the inhaler at all, instead it could be supplied separate to the inhaler, either being measured into the inhaler before use or by using a pre-metered dose pack. For example, the user could install a dose blister pack into the inhaler prior to use, the pack being pierced when the two parts are closed together. Alternatively the inhaler could be supplied with a dose pack in position ready for use. In either case the inhaler could be re-used by discarding the pack after inhalation and replacing it with a fresh one.

The invention claimed is:

1. A dry powder inhaler comprising two parts connected by an integrally moulded hinge configured to hinge the two parts of the inhaler from an open position to a closed position, at least one of said parts defining at least part of a circulating airflow chamber, wherein when said parts are in said closed position, the inhaler comprises an airflow path including the circulating airflow chamber, the inhaler further comprising a dose to be inhaled which is sealed in the at least part of the circulating airflow chamber by a frangible membrane and being arranged such that the frangible membrane is broken by an action of closing the inhaler prior to use and the dose is exposed to an entraining airflow in the circulating airflow chamber upon inhalation, and wherein the circulating airflow chamber having air and entrained substance particles circulate further comprises an axis and being elongate along said axis, an air inlet, a closed base and a vortex finder, said chamber being shaped wherein at least a part of the chamber decreases in cross-sectional area in a direction away from the air inlet, wherein the air inlet is configured to direct air to circulate around the periphery of the chamber, and the vortex finder is configured such that air exits therethrough after a reversal of axial direction at the base of the chamber to set up a reverse flow cyclone in the chamber wherein air circulates in two generally concentric overlapping columns in opposite axial directions.

2. An inhaler as claimed in claim 1 adapted for administration of a single dose of medicament powder and subsequent disposal.

3. An inhaler as claimed in claim 1 wherein the outer wall of the chamber tapers towards the base.

4. An inhaler as claimed in claim 1 wherein said chamber is generally frusto-conical.

5. An inhaler as claimed in claim 1 wherein the circulating airflow chamber is formed integrally with or permanently attached to one of the inhaler parts.

6. An inhaler as claimed in claim 1 comprising a mouthpiece formed integrally with one of the hinged parts.

7. An inhaler as claimed in claim 1 wherein the whole inhaler is integrally moulded in one piece.

8. An inhaler as claimed in claim 1 arranged such that an inhalation airflow path through the inhaler is only formed when the two parts are closed together.

9. An inhaler as claimed in claim 1 comprising one or more piercers on one of the parts; and the at least part of the circulating airflow chamber on the other part; wherein the dose is released by the act of closing the two parts of the inhaler together.

10. An inhaler as claimed in claim 1 comprising a main airflow path which passes through the circulating airflow chamber and a bypass airflow path bypassing the circulating airflow chamber; wherein the main and bypass airflow paths communicate with a mouthpiece.

11. An inhaler as claimed in claim 10 comprising a divided mouthpiece, with one channel for the main airflow and the other channel for the bypass airflow, such that the main and bypass airflows do not meet at all inside the inhaler.

12. An inhaler as claimed in claim 1 comprising a single dose of medicament powder.

13. An inhaler as claimed in claim 1 wherein an outlet pipe projects into the circulating airflow chamber to form the vortex finder.

14. An inhaler as claimed in claim 13 wherein the vortex finder is integrated with a piercer.

15. An inhaler as claimed in claim 1 wherein the diameter of the circulating airflow chamber is between 5 and 100 mm.

16. An inhaler as claimed in claim 1 comprising a snap fit closure.

17. An inhaler as claimed in claim 1 wherein the diameter of the circulating airflow chamber is between 5 and 50 mm.

18. An inhaler as claimed in claim 1 wherein the diameter of the circulating airflow chamber is between 8 and 20 mm.

19. A dry powder inhaler comprising two parts connected by an integrally moulded hinge configured to hinge the two parts of the inhaler from an open position to a closed position, at least one of said parts defining at least part of a circulating airflow chamber, wherein when said parts are in said closed position, the inhaler comprises an airflow path including the circulating airflow chamber, the inhaler further comprising a dose to be inhaled which is sealed in the at least part of the circulating airflow chamber by a frangible membrane and being arranged such that the frangible membrane is broken by an action of closing the inhaler prior to use and the dose is exposed to an entraining airflow in the circulating airflow chamber upon inhalation, the inhaler further comprising, at least when in its closed position: said circulating airflow chamber having an outlet extending substantially axially therefrom; a mouthpiece channel having a central axis; and a plenum portion connecting said outlet and said mouthpiece channel, the mouthpiece channel axis being offset from, and making a non-parallel angle with, an axis of the outlet such that air exits the outlet at least partly tangentially into the mouthpiece via the plenum portion.

\* \* \* \* \*